US010118884B2

United States Patent
Hallinan et al.

(10) Patent No.: US 10,118,884 B2
(45) Date of Patent: Nov. 6, 2018

(54) ACETIC ACID PROCESS

(71) Applicant: LyondellBasell Acetyls, LLC, Houston, TX (US)

(72) Inventors: Noel C. Hallinan, Loveland, OH (US);
David L. Ramage, Houston, TX (US);
David A. Heaps, Pearland, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 15/483,681

(22) Filed: Apr. 10, 2017

(65) Prior Publication Data

US 2017/0210690 A1    Jul. 27, 2017

Related U.S. Application Data

(63) Continuation-in-part of application No. 15/062,756, filed on Mar. 7, 2016, now Pat. No. 9,656,939.

(60) Provisional application No. 62/130,369, filed on Mar. 9, 2015.

(51) Int. Cl.
*C07C 51/12* (2006.01)
*G01N 21/65* (2006.01)

(52) U.S. Cl.
CPC ............ *C07C 51/12* (2013.01); *G01N 21/65* (2013.01)

(58) Field of Classification Search
None
See application file for complete search history.

(56) References Cited

U.S. PATENT DOCUMENTS

| | | |
|---|---|---|
| 6,362,366 B1 | 3/2002 | Hallinan et al. |
| 2012/0095259 A1* | 4/2012 | Salisbury ............... C07C 51/12 562/519 |
| 2012/0220801 A1 | 8/2012 | Salisbury et al. |
| 2016/0264502 A1 | 9/2016 | Hallinan et al. |

OTHER PUBLICATIONS

Pelletier ("Quantitative Analysis Using Ramen Spectrometry" Applied Spectroscopy, vol. 57, No. 1, 2003, p. 20A-42A). (Year: 2003).*
PCT/US2016/021179 International Search Report and Written Opinion dated Jun. 20, 2016.
Villanova University, Raman Spectroscopy, 37 pages, Feb. 11, 2013.

* cited by examiner

*Primary Examiner* — Jafar F Parsa
*Assistant Examiner* — Amy C Bonaparte

(57) ABSTRACT

The present disclosure provides for a method for measuring the concentration of one or more components in a reactor or a separation unit of an acetic acid process by Raman spectroscopic analyses. In some embodiments, the conditions in the reactor or in any subsequent step of the acetic acid production process are adjusted in response to the measured concentration of one or more components.

13 Claims, 2 Drawing Sheets

ACETIC ACID PROCESS

CROSS-REFERENCE TO RELATED APPLICATIONS

This application is a continuation-in-part of U.S. application Ser. No. 15/062,756, filed on Mar. 7, 2016, which claims the benefit of priority to U.S. Provisional Application No. 62/130,369, filed on Mar. 9, 2015, both of which are incorporated herein by reference in their entirety.

FIELD OF THE INVENTION

The present disclosure relates to an acetic acid preparation process. In some embodiments, the present disclosure relates to controlling an acetic acid production process by: (a) using Raman spectroscopy to measure the concentration of a reference component in a reactor mixture or a product stream with an uncoated probe; (b) using Raman spectroscopy to measure the concentration of a reference component and at least one other component in a reactor mixture or a product stream with a coated probe; and (c) correlating the Raman spectroscopy measurement obtained with the uncoated probe with the Raman spectroscopy measurements of components obtained with a coated probe in a reactor mixture or a product stream.

BACKGROUND OF THE INVENTION

Acetic acid is commercially produced from methanol and carbon monoxide by methanol carbonylation in the presence of water. The process may further contain methyl acetate as a co-feed. As an alternative to methyl acetate, the reaction can take place in the presence of a mixture of methyl acetate and methanol from byproduct streams of the hydrolysis/methanolysis of polyvinyl acetate. Various techniques can be used to determine the components of the reaction mixture and to modify the process.

SUMMARY OF THE INVENTION

In some embodiments, the present disclosure provides a method for measuring the concentration of one or more components in a reactor or a separation unit of the acetic acid process by Raman spectroscopic analyses and adjusting the conditions in the reactor or in any subsequent step of the acetic acid production process in response to the measured concentration. In certain embodiments of this disclosure, no dependence on any external analytical technique. In addition, embodiments of this disclosure provide real-time, quantitative determinations of signal decrease.

In another embodiment, the present disclosure provides for a method for producing acetic acid comprising:
(A) reacting, in a carbonylation reactor and the presence of a carbonylation catalyst,
  (i) methanol,
  (ii) carbon monoxide, and
  (iii) water,
  to produce a reactor mixture;
(B) measuring an initial value for a reference component by Raman spectroscopic analysis with a probe or flow-through cell in contact with the reactor mixture, wherein the probe or flow-through cell is uncoated;
(C) measuring a value for the reference component and measuring the concentration of one or more components of interest in the reactor mixture by Raman spectroscopic analysis;
(D) determining an Adjustment Ratio by dividing the initial value for the reference component by the value for the reference component;
(E) calculating an Adjusted Value for the concentration of the component(s) of interest by multiplying the concentration of the component(s) of interest by the Adjustment Ratio; and
(F) modifying at least one process condition in the carbonylation reactor or a separation unit, based upon the Adjusted Value.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE DRAWINGS

Further details will be apparent from the following detailed description, with reference to the enclosed drawings, in which.

DETAILED DESCRIPTION OF THE INVENTION

Figure 1:
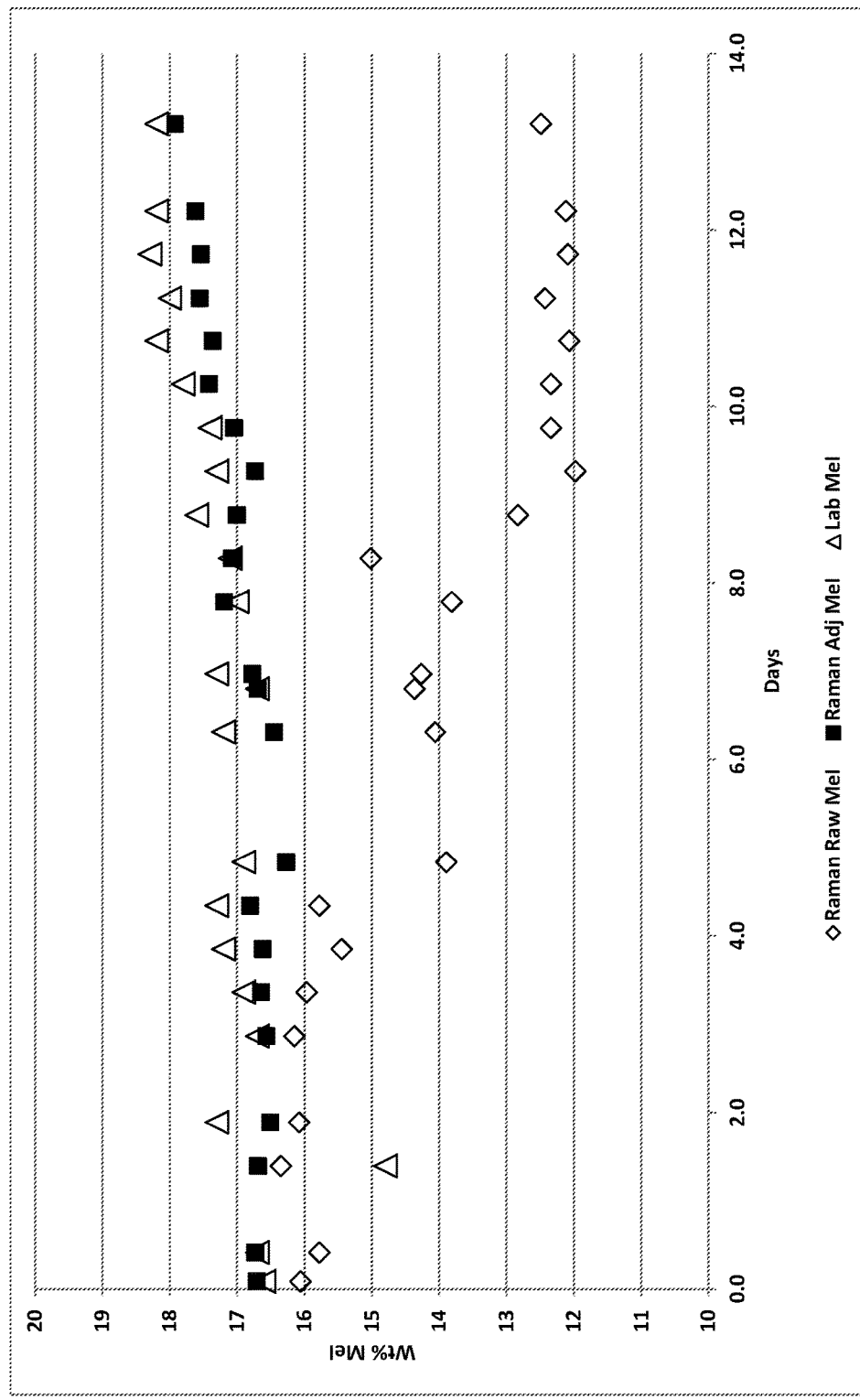
FIG. 1 is a graph showing time-lapse concentration measurements of methyl iodide in a methanol carbonylation process.

The present disclosure now will be described more fully. However, this technology may be embodied in many different forms and should not be construed as limited to the embodiments set forth herein. As such, it will be apparent to those skilled in the art that the embodiments may incorporate changes and modifications without departing from the general scope of the disclosure. It is intended to include all such modifications and alterations in so far as they come within the scope of the appended claims or the equivalents thereof.

As used in this specification and the claims, the singular forms "a," "an," and "the" include plural referents unless the context clearly dictates otherwise.

As used in this specification and the claims, the terms "comprising," "containing," or "including" mean that at least the named compound, element, material, particle, method step, etc., is present in the composition, the article, or the method, but does not exclude the presence of other compounds, elements, materials, particles, method steps, etc., even if the other such compounds, elements, materials, particles, method steps, etc., have the same function as that which is named, unless expressly excluded in the claims. It is also to be understood that the mention of one or more method steps does not preclude the presence of additional method steps before or after the combined recited steps or intervening method steps between those steps expressly identified.

Moreover, it is also to be understood that the lettering of process steps or ingredients is a convenient means for identifying discrete activities or ingredients and the recited lettering can be arranged in any sequence, unless expressly indicated.

For the purpose of the present description and of the claims which follow, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

Some embodiments include the production of glacial acetic acid, which is encompassed by the term "acetic acid" as used herein. Glacial acetic acid typically refers to acetic acid that is undiluted, generally meaning that the acetic acid has a water concentration of about 0.15 wt % or less, based on the total weight of acetic acid and water.

Acetic acid is commercially produced from methanol and carbon monoxide by methanol carbonylation in the presence of water. The process may further contain methyl acetate as a co-feed. As an alternative to methyl acetate as a co-feed, the reaction can take place in the presence of a mixture of methyl acetate and methanol from byproduct streams of the hydrolysis/methanolysis of polyvinyl acetate. Additionally, methyl acetate may be generated during the process. Such carbonylation processes can use carbonylation catalyst systems based on (a) rhodium or (b) iridium, with or without a catalyst stabilizer or a catalyst promoter.

When the catalyst comprises rhodium, the catalyst can be rhodium metal or a rhodium compound. The rhodium compounds can be selected from the group consisting of rhodium salts, rhodium oxides, rhodium acetates, organo-rhodium compounds, coordination compounds of rhodium and mixtures thereof. Specific examples of rhodium compounds include $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ and $[H]Rh(CO)_2I_2$.

When the catalyst is based on iridium, the catalyst may comprise iridium metal or an iridium compound. The iridium compounds can be selected from the group consisting of iridium salts, iridium oxides, iridium acetates, iridium oxalates, iridium acetoacetates, coordination compounds of iridium and mixtures thereof. Specific examples of iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$ and $H_2[IrCl_6]$.

In general, there are two types of catalyst stabilizers. The first type of catalyst stabilizer is a metal iodide salt such as lithium iodide. The second type of catalyst stabilizer is a non-salt stabilizer, including pentavalent Group VA oxides such as phosphine oxides.

An example of a catalyst promoter is methyl iodide. Methyl iodide may be added directly to the process or generated by adding hydrogen iodide to the process.

As previously noted, methanol and carbon monoxide are fed to the carbonylation reactor. It is believed that the methanol does not react directly with the carbon monoxide to form acetic acid. Instead, it is first converted to methyl acetate by reaction with acetic acid. Methyl acetate is then converted to methyl iodide by the hydrogen iodide present in the acetic reactor. Methyl iodide is then reacted with carbon monoxide and water to give acetic acid and regenerate the hydrogen iodide.

The carbonylation reaction can be performed at a temperature within the range of about 150 degrees Celsius (° C.) to about 250 ° C. and under a pressure within the range of about 200 psig (1380 kPa) to about 2,000 psig (13,800 kPa).

After the carbonylation reaction, the reaction mixture is passed downstream to one or more separation units. Separation units may be a vessel or step in an acetic acid process which separates a feed stream into two or more separate exit streams where the two exit streams differ from one another in some aspect. The separation can be based on methods such as separation by physical characteristics (e.g., density, volatility, boiling point, phase, absorbance, and adsorbance) and other characteristics used for separating chemical components known to the skilled artisan.

The separation units can include, but are not limited to, a flash tank, a light ends distillation column, a decanter, a drying column, a heavy ends distillation column and combinations thereof.

In a flash tank, the acetic acid product stream is withdrawn from the reactor and separated into (a) a liquid fraction containing the catalyst and the catalyst stabilizer and (b) a vapor fraction containing the acetic acid product, the reactants, water, methyl iodide, and impurities generated during the carbonylation reaction including acetaldehyde. The liquid fraction can be recycled to the carbonylation reactor. The vapor fraction is then passed to a distillation column.

In a light ends distillation column, the vapor fraction is separated based upon boiling point into at least (a) an overhead fraction containing methyl iodide, water, methanol, methyl acetate, acetic acid, alkanes and acetaldehyde and (b) an acetic acid stream containing acetic acid, water, hydrogen iodide and heavy impurities such as propionic acid.

In a decanter, the overhead fraction is condensed and separated by density to (a) a lighter aqueous phase and (b) a heavier organic phase. The lighter aqueous phase can contain one or more of water, acetic acid, methyl acetate, methyl iodide, acetaldehyde and alkanes and have a density of about 1.0 grams per cubic centimeter to about 1.10 grams per cubic centimeter. Like the lighter aqueous phase, the heavier organic phase can contain water, acetic acid, methyl acetate, methyl iodide, acetaldehyde and alkanes; the organic phase may further comprise higher concentrations of methyl iodide and alkanes. The heavier organic phase can have a density of about 1.4 grams per cubic centimeter to about 2.2 grams per cubic centimeter. The lighter aqueous phase can be recycled to the reactor or to the light ends distillation column.

In a drying column, the residual water is removed from the acetic acid stream. In a heavy ends distillation column, the heavy impurities are removed from the acetic acid stream.

In some embodiments, a method for measuring the various acetic acid stream components is performed using Raman spectroscopy method such as an online Raman spectroscopy method. A Raman probe can be inserted directly into the reactor solution or may be inserted into a reactor slipstream. In the case of a slipstream, continuous flow can be employed, and the reactor solution can be returned to the reaction system. Instead of a probe, a flow through cell equipped with windows may also be used to monitor a slipstream. The use of a back pressure regulator or similar device can prevent a pressure drop across the cells, thereby ensuring analyses are performed with minimal change from the reactor pressure and there is no degassing or bubble formation in the cells.

The temperature of the slipstream can be maintained anywhere between ambient and process temperature, for instance about 150° C., about 175° C. and about 200° C. Selection of the temperature depends on several parameters, such as precipitation of solids, compatibility of the cell window or crystal materials with process conditions and controlling the process reaction in the slipstream.

All tubing, valving and the like contacting the reaction solution must be chemically inert to the reaction components and be capable of withstanding corrosive attack under the reaction conditions. Suitable manufacturing materials for use in the tubes, valves, and similar equipment include HASTELLOY™ B2 Ni—Mo—Fe alloy, HASTELLOY™ B3 Ni—Mo—Fe alloy and zirconium.

A method for measuring the various components in the reactor mixture is online Raman spectroscopy. This Raman method provides measurements that can be used to adjust the reaction system. A Raman shift occurs when light impinges upon a molecule and interacts with the electron cloud and the bonds of that molecule. It is believed that a photon excites the molecule from the ground state to a virtual energy state and that when the molecule relaxes, the molecule emits a photon and returns to a different rotational or vibrational state. The difference in energy between the original state and the new state leads to a shift in the emitted photon's frequency away from the excitation wavelength. Raman spectra can be shown as plots of signal strength or peak intensity (arbitrary units) versus Raman shift. Raman shifts can be expressed in wavenumbers, which have units of inverse length such as inverse centimeters ($cm^{-1}$).

The instrumentation used to collect and process Raman data includes a Raman spectrometer system, a transmittance system, a control loop and a processor. The Raman spectrometer system comprises a Raman spectrometer, with its principal components being a light source, a monochromator and a detector. The light source delivers excitation radiation to the probe, where scattered radiation is collected, filtered of Raleigh scattered light and dispersed via a monochromator. The dispersed Raman scattered light is then imaged onto a detector and subsequently processed within the processor.

The light source can be a visible laser, such as a frequency-doubled Nd:YAG laser (532 nm), a helium-neon laser (633 nm) or a solid-state diode laser (785 nm). The laser can be a pulsed or continuous wave (CW) laser, polarized as desired or randomly polarized, or single-mode. Light sources other than lasers can be used. The excitation radiation can be delivered to the probe, and the scattered radiation can be collected from the probe.

The scattered radiation of the carbonylation reaction mixture may be collected by a probe in a variety of locations in one or more of the separations units. The probe may be placed directly in a vessel, a feed stream entering or exiting the unit or a slipstream. An issue with Raman probes and flow-through cells is that their external surfaces can become coated over time with one or more chemicals from the reactor mixture. The coating of the cell window or the probe will lead to a decrease in signal reaching the detector, with an associated decrease in observed component concentration values. As such, the coating can significantly impact the accuracy of the measurements and impede process control.

In certain embodiments, the initial Raman spectroscopic measurement of the reference component is obtained with an uncoated probe or flow-through cell. As such, the probe and/or flow-through cell has no build-up or deposits thereon that interfere with or decrease the signal transmitted to the Raman detector. As used throughout this document, the term "coated" encompasses any coating or deposit that negatively affects (decreases) the amount of radiation collected by the Raman probe. Analogously, as used throughout this document, the term "uncoated" refers to a Raman probe which does not experience a decrease in the amount of radiation collected.

For online Raman process measurement, fiber optic cables can be used to deliver the excitation radiation and collect the scattered radiation. The use of fiber optic cables facilitates positioning the excitation source remotely from the sampling region, providing an environmental advantage for Raman spectroscopy over infrared systems.

The collected scattered radiation is filtered to remove Raleigh scattering and frequency (wavelength) dispersed using a suitable dispersive element or interferometrically. The monochromator can be any such dispersive element, along with associated filters and beam manipulation optics. The dispersed Raman scattering is imaged onto a detector. Detectors can include array detectors or single element detectors. If array detectors are used, the detector is calibrated such that the frequency (wavelength) corresponding to each detector element is known. The detector response is delivered to the processor that generates a set of frequency shift, intensity (x,y) data points which constitute the Raman spectrum. Raman spectroscopy can measure compounds such as water, acetic acid, hydrogen iodide, methyl iodide, methyl acetate, acetaldehyde, pentavalent phosphine oxides such as triphenyl phosphine oxide and a mixture of four trialkyl phosphine oxides in which the alkyl groups are n-hexyl and n-octyl (Cytop® 503; formerly Cyanex® 923; Cytec Industries, Inc.), and dissolved carbon monoxide.

In various embodiments, concentrations are determined from the signal strengths or peak intensities of the Raman spectroscopic measurements. The concentrations determined from the Raman spectroscopic measurements are used to adjust (modify) one or more process conditions in the carbonylation reactor or a separation unit.

In a general embodiment, the present disclosure provides a method for measuring the concentration of one or more components of interest in the reactor or a separation unit of the acetic acid process by Raman spectroscopic analysis and then adjusting the conditions in the reactor or in any subsequent step of the acetic acid production process in response to the Adjusted Value concentration of the component(s) of interest. An Adjusted Value concentration of a measured component of interest is generally more accurate, as any changes in measured component concentration from spectrum to spectrum are from a combination of actual concentration change and any change in extent of probe coating.

As previously noted, Raman spectroscopy can measure water, acetic acid, hydrogen iodide, methyl iodide, methyl acetate, acetaldehyde, pentavalent phosphine oxides such as triphenyl phosphine oxide (TPPO) and Cytop® 503, and dissolved carbon monoxide. Of the components that can be measured by Raman spectroscopic analysis, the reference component is usually glacial acetic acid (GAA), a pentavalent phosphine oxide, or the Raman Total Signal Strength.

Examples of process condition adjustments include increasing or decreasing the temperature or the pressure of the reactor or separation unit(s). Additionally, the flow rates of the feeds or exit streams can be increased or decreased. Such adjustments can affect the concentrations of one or more components in the reactor or a separations unit to bring the components within a desired range. For instance, the concentration of methyl iodide and the catalyst can determine the reaction rate. The concentration of the pentavalent phosphine oxide may affect catalyst stability and reaction rate. The concentration of methyl acetate may be correlated to the percentage of catalyst being used for carbonylation (i.e., the amount of idle catalyst). The presence of water drives the formation of acetic acid, as water is used in the final step of the catalytic process. The dissolved carbon monoxide assists in catalyst regeneration and is a product of a water-gas-shift reaction.

In the present disclosure, Raman spectroscopy permits the calculation of accurate methyl iodide and methyl acetate concentrations. Methyl iodide has a strongly-scattering, characteristic peak in the Raman spectrum, and advantageously there is low interference from any other reactor solution components. Additionally, water and acetic acid Raman peaks permit accurate determination of their concentrations without interfering with peaks for methyl iodide or methyl acetate. In addition, pentavalent phosphine oxides, which include TPPO and Cytop® 503, can also be accurately measured by Raman spectroscopy.

As previously noted, an issue with Raman probes and flow-through cells is that their external crystal structures can become coated over time because the probe and/or flow-through cell is in contact with the reactor mixture. The coating of the cell window or the probe crystal will lead to a decrease in signal reaching the detector and an associated decrease in measured component concentration values. As such, the coating can adversely impact the accuracy of the probes and impede process control. The present disclosure advantageously increases the accuracy of Raman spectroscopic measurements by correlating Raman measurements of certain (reference) components to measurements obtained when the Raman probe and/or flow-through cell was uncoated (initial measurements).

One such reference component, the (Raman) Total Signal Strength, is measured by the Raman intensity on the y-axis of a Raman spectrum. The Total Signal Strength is largely uninfluenced by actual changes in concentrations of the reactor solution components, but decreases or increases as the Raman probe or flow-through cell becomes coated (or uncoated).

An additional reference component is one of the reactor solution components whose actual concentration remains largely at steady state and whose measurement for process control purposes is not required. In this case, any changes in the peak intensity of the signal associated with this component can be attributed to changes in probe coating. Reactor GAA concentration may remain at close to steady state for long periods, and thus GAA can be used as a reference component. When significant actual change in GAA concentration is expected, the Total Signal Strength can be used as the reference component. Another reference component is an involatile catalyst stabilizer such as a pentavalent phosphine oxide (e.g., TPPO), because the concentration of such stabilizers remain at close to steady state.

The present disclosure provides for a method for using the ratio (Adjustment Ratio) of (a) an initial Raman measurement for a reference component (Reference$_{initial}$) and (b) the contemporaneous (raw) Raman measurement obtained for the reference component (Reference$_{contemp}$), to adjust the Raman values for each component of interest (Component$_{Adjusted}$). The equation to calculate the Adjustment Ratio is shown below:

$$\text{Adjustment Ratio} = \text{Reference}_{initial}/\text{Reference}_{contemp}$$

The initial concentration of the reference component is a fixed value, and the contemporaneous (raw) concentration of the reference component varies from spectrum to spectrum. As noted above, the reference component can be Total Signal Strength or any reactor solution component whose concentration remains close to steady state (e.g., GAA or a pentavalent phosphine oxide).

Similarly, the raw (contemporaneous) concentration of a component of interest varies from spectrum to spectrum. The Adjustment Ratio permits accurate determination of concentrations for components that are readily measured by Raman spectroscopy, such as water, acetic acid, hydrogen iodide, methyl iodide, methyl acetate, acetaldehyde, a pentavalent phosphine oxide such as TPPO and dissolved carbon monoxide. The equation to calculate the adjusted concentration of a component of interest is shown below.

$$\text{Component}_{Adjusted} = (\text{Adjustment Ratio}) * \text{Component}_{contemp}$$

Again, as noted above, Component$_{contemp}$ is the raw (contemporaneous) measured concentration of a component of interest where the measurement value is associated with actual component concentration and with extent of probe coating. Component$_{Adjusted}$ is the accurate value of component concentration where the raw value is adjusted based on any changes in probe coating. The raw or unadjusted Raman measurements for both the reference component and the components of interest may be recorded contemporaneously (in the same Raman spectrum) Alternatively, measurement of the raw reference component and measurement of the raw components of interest may be performed as close together in time as permitted.

Another way of expressing the calculation to determine the Adjusted Value concentration of a component of interest is shown by the following equation:

$$\text{Component}_{Adjusted} = (\text{Reference}_{initial}/\text{Reference}_{contemp}) * \text{Component}_{contemp}$$

An advantage of some of the embodiments of this disclosure is that a single analyzer may be used, which in turn minimizes errors in comparison to other methods, such as those that require more than one analyzer, while maintaining good process control. Another advantage of some of the embodiments of this disclosure is that an external reference is unnecessary for adjustment calculations.

In one embodiment, the method can be performed instantly or in real time. In a general embodiment, the present disclosure provides for a method for the production of acetic acid containing the steps of:

(A) reacting, in a carbonylation reactor and the presence of a carbonylation catalyst, ingredients comprising:
   (i) methanol,
   (ii) carbon monoxide, and
   (iii) water,
   to produce a reactor mixture;
(B) measuring an initial value for a reference component by Raman spectroscopic analysis with a probe or flow-through cell in contact with the reactor mixture, wherein the probe or flow-through cell is uncoated;
(C) measuring a contemporaneous value for the reference component and measuring the concentration of one or more components of interest in the reactor mixture by Raman spectroscopic analysis;
(D) determining an Adjustment Ratio by dividing the initial value for the reference component by the contemporaneous value for the reference component;
(E) calculating an Adjusted Value for the concentration of the component(s) of interest by multiplying the contemporaneous concentration of the component(s) of interest by the Adjustment Ratio; and
(F) modifying at least one process condition in the carbonylation reactor or a separation unit, based upon the Adjusted Value.

The ingredients can further include methyl acetate, a catalyst stabilizer, a catalyst promoter and/or hydrogen iodide. As previously noted, there are two types of catalyst stabilizers in general. The first type of catalyst stabilizer is metal iodide salt such as lithium iodide. The second type of catalyst stabilizer is a non-salt stabilizer, including pentavalent Group VA oxides such as phosphine oxides (e.g., triphenyl phosphine oxide). An example of a catalyst promoter is methyl iodide. Methyl iodide may be added directly to the process or generated by adding hydrogen iodide to the process. The reactor mixture can include the carbonylation catalyst, methanol, methyl acetate, water, carbon monoxide, carbon dioxide, methyl iodide, or acetic acid.

Another way of determining whether the probe and/or flow-through cell is coated or uncoated is via the Adjustment Ratio. When the Adjustment Ratio is about 0.01 or below, the probe and/or flow-through cell is considered to be uncoated. In an analogous manner, the probe and/or flow-through cell is considered to be coated when the Adjustment Ratio is above 0.01.

In some embodiments, the Raman probe and/or flow-through cell can become sufficiently coated as to render inappropriate any further use of an Adjustment Ratio to calculate an Adjusted Value. The situation may arise when the probe has a signal of 20% or less. As such, when the Adjustment Ratio is about 5 or greater, the Raman probe should be cleaned. In some embodiments, the Adjustment Ratio is has a value of less than about 5. In some embodiments, the Adjustment Ratio is has a value of 0.01 to about 5. Examples of process conditions that can be modified include the temperature of the carbonylation reactor, the pressure of the carbonylation reactor, a temperature of a separation unit, a pressure of a separation unit, a flow rate of an ingredient, a flow rate of an exit stream, the concentration of a component, and the selection of a component.

EXAMPLES

The following example is included to demonstrate certain embodiments of the technology. It should be appreciated by those of skill in the art that many changes can be made in the specific embodiments described herein and still obtain similar results without departing from the spirit and scope of the disclosure.

Data in this example were obtained from a continuous methanol carbonylation unit equipped with a reactor, a flash tank, a light ends distillation column, a decanter, a drying column and a flow-through cell containing a Raman probe. A reactor solution slipstream was continuously passed in series through the flow-through cells and returned to the process via the flash tank. The flow-through cell was maintained at about the temperature and the pressure of the reactor, which were about 175° C. and 400 psig (2760 kPa), respectively.

The flow-through cell contained a Kaiser Optical Systems fiber optically-coupled Raman probe with a sapphire crystal. The parts of the probe that were in contact with the reactor solution were constructed of HASTELLOY™ B2 alloy.

The Examples pertain to a time period of about 13 days of continuous operation during which the Raman probe became heavily coated with solid material. The reactor solution contained components present in a methanol carbonylation process such as water, methyl acetate, rhodium catalyst, triphenyl phosphine oxide, acetic acid and methyl iodide.

The trend lines in FIG. 1 show that methyl iodide (MeI) concentration as determined by Raman signal strength measurement agree closely for the first few days of the time period. Subsequently, the contemporaneous (raw) Raman-measured MeI concentrations decrease significantly. In FIG. 1, the raw Raman measurements are plotted along with the corresponding adjusted values. The Adjustment Ratio values were obtained from the equation shown above and reproduced below in which MeI is the component to be adjusted.

$$Component_{Adjusted} = (Reference_{initial}/Reference_{contemp}) * Component_{contemp}$$

For this run, GAA was the reference component and its initial concentration was measured with a clean (uncoated) probe. The actual GAA concentration remained close to steady state over the 13-day operating period, as determined by off-line gas chromatography (GC) analysis, which showed a concentration range of 56±2 wt %. Thus, any changes in raw GAA concentration as measured by Raman can be attributed to probe coating and the specific equation for this MeI measurement is:

$$MeI_{Adjusted} = (GAA_{initial}/GAA_{contemp}) * MeI_{contemp}$$

Table 1 below shows the raw and adjusted Raman-measured MeI values at the same time points where the reactor was sampled for GC analysis of GAA in the lab. From FIG. 1, it should be noted that the Raman-measured raw MeI concentration dropped by over 40% of its initial value and thus any error in the adjustment associated with the small actual variation in GAA concentration is very small in comparison.

Figure 2:
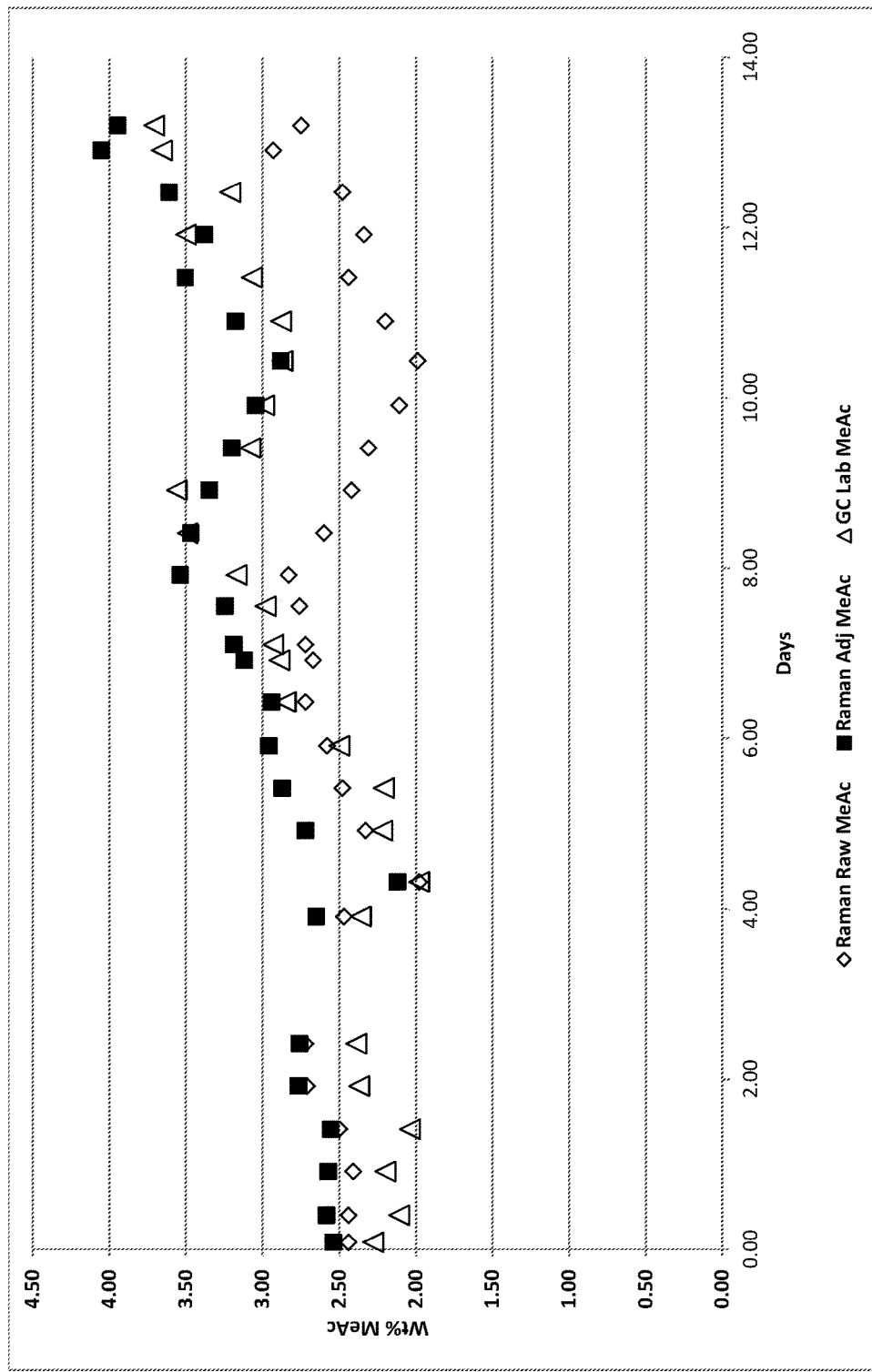
FIG. 2 is a graph showing time-lapse concentration measurements of methyl acetate in a methanol carbonylation process.

In a similar manner, FIG. 2 shows trend lines for methyl acetate (MeAc) concentration as determined by Raman signal strength measurement. For MeAc, in FIG. 2, the raw Raman measurements are plotted along with the corresponding adjusted values. The Adjustment Ratio values were obtained from the equation shown above and reproduced below in which MeAc is the component to be adjusted.

$$Component_{Adjusted} = (Reference_{initial}/Reference_{contemp}) * Component_{contemp}$$

For this run, GAA was the reference component and its initial concentration was measured with a clean (uncoated) probe. The actual GAA concentration remained close to steady state over a 13-day operating period, as determined by off-line GC analysis, which showed a concentration range of 56±2 wt %. Thus, any changes in raw GAA concentration as measured by Raman can be attributed to probe coating. The specific equation for this MeAc measurement is:

$$MeAc_{Adjusted} = (GAA_{initial}/GAA_{contemp}) * MeAc_{contemp}$$

Table 2 below shows the raw and adjusted Raman-measured MeAc values at the same time points where the reactor was sampled for GC analysis of GAA in the lab. From FIG. 2, it should be noted that the Raman-measured raw MeAc concentration dropped by over 40% of its initial value and thus any error in the adjustment associated with the small actual variation in GAA concentration is very small in comparison.

TABLE 1

| Days | MeI Raw (Raman) | MeI Adj (Raman) | MeI Lab (GC) |
|---|---|---|---|
| 0.08 | 16.06 | 16.71 | 16.6 |
| 0.41 | 15.78 | 16.73 | 16.7 |
| 1.39 | 16.35 | 16.69 | 14.8 |
| 1.89 | 16.08 | 16.51 | 17.3 |
| 2.86 | 16.15 | 16.57 | 16.7 |
| 3.36 | 15.97 | 16.65 | 16.9 |
| 3.85 | 15.45 | 16.62 | 17.2 |
| 4.34 | 15.78 | 16.81 | 17.3 |
| 4.83 | 13.89 | 16.27 | 16.9 |

TABLE 1-continued

| Days | MeI Raw (Raman) | MeI Adj (Raman) | MeI Lab (GC) |
|---|---|---|---|
| 6.31 | 14.06 | 16.45 | 17.2 |
| 6.80 | 14.37 | 16.70 | 16.7 |
| 6.97 | 14.27 | 16.78 | 17.3 |
| 7.78 | 13.81 | 17.20 | 17 |
| 8.28 | 15.02 | 17.08 | 17.1 |
| 8.77 | 12.83 | 17.01 | 17.6 |
| 9.26 | 11.98 | 16.74 | 17.3 |
| 9.75 | 12.34 | 17.05 | 17.4 |
| 10.25 | 12.34 | 17.42 | 17.8 |
| 10.74 | 12.07 | 17.36 | 18.2 |
| 11.23 | 12.43 | 17.56 | 18 |
| 11.72 | 12.09 | 17.54 | 18.3 |
| 12.21 | 12.12 | 17.62 | 18.2 |
| 13.20 | 12.49 | 17.93 | 18.2 |

FIG. 1 is a graphical plot of the data presented above in Table 1. FIG. 1 shows that the adjusted Raman MeI values and the offline GC MeI values agree, while the raw MeI values decreased over time.

TABLE 2

| Days | MeAc Raw (Raman) | MeAc Adj (Raman) | MeAc Lab (GC) |
|---|---|---|---|
| 0.08 | 2.44 | 2.54 | 2.28 |
| 0.40 | 2.44 | 2.58 | 2.11 |
| 0.92 | 2.41 | 2.57 | 2.2 |
| 1.41 | 2.5 | 2.56 | 2.04 |
| 1.92 | 2.71 | 2.77 | 2.37 |
| 2.41 | 2.72 | 2.76 | 2.39 |
| 3.91 | 2.47 | 2.65 | 2.36 |
| 4.32 | 1.98 | 2.12 | 1.98 |
| 4.92 | 2.33 | 2.72 | 2.22 |
| 5.42 | 2.48 | 2.87 | 2.21 |
| 5.91 | 2.58 | 2.96 | 2.5 |
| 6.43 | 2.72 | 2.94 | 2.85 |
| 6.92 | 2.67 | 3.12 | 2.89 |
| 7.10 | 2.72 | 3.19 | 2.93 |
| 7.55 | 2.76 | 3.25 | 2.98 |
| 7.92 | 2.83 | 3.54 | 3.17 |
| 8.41 | 2.6 | 3.47 | 3.49 |
| 8.91 | 2.42 | 3.35 | 3.56 |
| 9.41 | 2.31 | 3.20 | 3.08 |
| 9.92 | 2.11 | 3.05 | 2.99 |
| 10.43 | 1.99 | 2.88 | 2.87 |
| 10.90 | 2.2 | 3.18 | 2.88 |
| 11.41 | 2.44 | 3.51 | 3.07 |
| 11.92 | 2.34 | 3.38 | 3.5 |
| 12.41 | 2.48 | 3.61 | 3.21 |
| 12.91 | 2.93 | 4.05 | 3.66 |
| 13.20 | 2.75 | 3.95 | 3.71 |

FIG. 2 is a graphical plot of the data presented above in Table 2. FIG. 2 shows that the adjusted Raman MeAc values and the offline GC MeAc values agree, but after a period of time, the raw MeAc values were lower than the adjusted values.

Although the present technology and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, compositions of matter, means, methods and steps described in the specification. As one of ordinary skill in the art will readily appreciate from the present disclosure, processes, machines, manufacture, compositions of matter, means, methods and/or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods and/or steps.

What is claimed is:

1. A method for the production of acetic acid comprising:
    (A) reacting,
        (i) methanol,
        (ii) carbon monoxide, and
        (iii) water,
        in a carbonylation reactor in the presence of a carbonylation catalyst to produce a reactor mixture;
    (B) measuring a first value for a reference component selected from the group consisting of glacial acetic acid (GAA), a pentavalent phosphine oxide, triphenyl phosphine oxide (TPPO), a catalyst promoter, a catalyst stabilizer, water, acetic acid, hydrogen iodide, methyl iodide, methyl acetate, acetaldehyde and carbon monoxide by Raman spectroscopic analysis with an uncoated probe or flow-through cell in contact with the reactor mixture;
    (C) measuring a second value for the reference component and measuring the concentration of one or more components of interest selected from the group consisting of glacial acetic acid (GAA), a pentavalent phosphine oxide, a catalyst promoter, a catalyst stabilizer, water, acetic acid, hydrogen iodide, methyl iodide, methyl acetate, acetaldehyde and carbon monoxide in the reactor mixture by Raman spectroscopic analysis;
    (D) determining an Adjustment Ratio by dividing the first value for the reference component by the second value for the reference component;
    (E) calculating an Adjusted Value for the concentration of the component(s) of interest by multiplying the concentration of the component(s) of interest by the Adjustment Ratio; and
    (F) modifying at least one process condition in the carbonylation reactor or a separation unit selected from the group consisting of temperature, pressure, component of interest concentration, feed stream flow rate and exit stream flow rate;
    wherein the Adjustment Ratio is maintained at a value of 0.01-5.

2. The method of claim 1, wherein the catalyst stabilizer is a pentavalent Group VA oxide.

3. The method of claim 1, wherein the catalyst promoter is methyl iodide.

4. The method of claim 3, wherein the reactor mixture comprises:
    (A) a carbonylation catalyst;
    (B) methanol;
    (C) methyl acetate;
    (D) water;
    (E) carbon monoxide;
    (F) carbon dioxide;
    (G) acetic acid; and
    (H) methyl iodide.

5. The method of claim 1, wherein the reactor mixture comprises:
    (A) a carbonylation catalyst;
    (B) methanol;
    (C) methyl acetate;
    (D) water;
    (E) carbon monoxide;
    (F) carbon dioxide;

(G) methyl iodide;
(H) acetic acid; and
(I) hydrogen iodide.

6. The method of claim 5, wherein the reaction mixture further comprises a phosphine oxide.

7. The method of claim 1, wherein the Adjustment Ratio is less than 5.

8. The method of claim 1, wherein the at least one process condition is selected from the group consisting of:
   (A) the temperature of the carbonylation reactor;
   (B) the pressure of the carbonylation reactor;
   (C) the temperature of the separation unit;
   (D) the pressure of the separation unit;
   (E) the feed stream flow rate of a component of interest;
   (F) the flow rate of an exit stream;
   (G) the concentration of a component of interest; and
   (H) the selection of a component of interest.

9. The method of claim 1, wherein the reference component is measured as a function of Raman Total Signal Strength as measured by the Raman signal intensity on the y-axis of a Raman spectrum.

10. The method of claim 1, wherein the temperature range of the carbonylation reactor is about 150° C. to about 250° C.

11. The method of claim 1, wherein the pressure range of the carbonylation reactor is about 1380 kPa to about 13,800 kPa.

12. The method of claim 1, wherein the carbonylation catalyst comprises rhodium or iridium.

13. The method of claim 1, wherein the uncoated probe produces a signal of at least 20%.

* * * * *